United States Patent [19]

Bohn

[11] 4,301,064

[45] Nov. 17, 1981

[54] UBIQUITARY TISSUE PROTEIN PP$_8$

[75] Inventor: Hans Bohn, Marburg an der Lahn, Fed. Rep. of Germany

[73] Assignee: Behringwerke Aktiengesellschaft, Marburg an der Lahn, Fed. Rep. of Germany

[21] Appl. No.: 79,589

[22] Filed: Sep. 27, 1979

[30] Foreign Application Priority Data

Sep. 29, 1978 [DE] Fed. Rep. of Germany ....... 2842467

[51] Int. Cl.$^3$ ............................................... C07G 7/00
[52] U.S. Cl. ............................ 260/112 R; 260/112 B; 424/85; 424/88; 424/95; 424/101; 424/103; 424/104; 424/105; 424/106; 424/110
[58] Field of Search ....................... 260/112 R, 112 B; 424/85, 88, 95, 105, 103, 104, 106, 110, 101

[56] References Cited

U.S. PATENT DOCUMENTS 3,931,399 1/1976 Bohn et al. ........................... 424/105
4,191,533 3/1980 Bohn et al. ................... 260/112 B X
4,217,339 8/1980 Bohn et al. ................... 260/112 R X
4,254,021 3/1981 Bohn et al. ....................... 260/112 R

OTHER PUBLICATIONS

Chem. Abstracts, vol. 86 (1977), 135224x, Bohn et al.
Chem. Abstracts, vol. 55, 23724f (1961), Centonze et al.
Chem. Abstracts, vol. 87 (1977) 163085s, Bohn.
Chem. Abstracts, vol. 77 (1972), 162901m, Bohn.
Protides of Biological Fluids, 24th Colloquium, Brugge 1976, Peeters, pp. 117-124.

*Primary Examiner*—Howard E. Schain
*Attorney, Agent, or Firm*—Curtis, Morris & Safford

[57] ABSTRACT

A new soluble tissue protein (PP$_8$) and a process for isolating it from human organs is described. The protein has antigenic properties. In the case of diseases which involve tissue disintegration its presence in the blood in increased concentration can be established.

2 Claims, No Drawings

UBIQUITARY TISSUE PROTEIN PP$_8$

The invention relates to a soluble tissue protein (PP$_8$) and to a process for isolating it from organ tissues, preferably from placentas.

PP$_8$ is found in almost all of the organs investigated up to now, especially in the placenta of humans. Its presence was established in the following fetal organs: heart, liver, kidneys, lungs, stomach, brain. Its presence was also established in the following adult organs: heart, lungs, stomach, kidneys, uterus, liver, spleen, adrenal gland, colon and bladder. In general, about 10 mg of this protein can be extracted with a physiological salt solution from a human grown placenta (600 g). The concentration of PP$_8$ in other human organs is assumed to be of similar magnitude. In the serum, PP$_8$ is normally present in traces only (<0.1 mg per 100 ml) or not at all.

An object of the invention is the provision of tissue protein PP$_8$, which is characterized by (a) a protein proportion of 96±3%, a content of carbohydrates of 4.1±0.95%, of which are 3.15±0.5% hexoses, 0.61±0.2% hexoseamine, 0.11±0.05% fucose and 0.23±0.20% neuraminic acid;

(b) a sedimentation coefficient $S_{20,W}$ of 3.7±0.3 S;

(c) a molecular weight of 45 000±5 000 determined in an ultracentrifuge;

(d) a molecular weight of 55 000±5 000 determined in sodium dodecylsulfate (SDS)-containing polyacrylamide gel;

(e) an extinction coefficient $E_1$ $_{cm}$1% (280 nm) of 8.1±1.0;

(f) an electrophoretic mobility in the range of the alpha $_1$- globulins; and (g) an isoelectric point of 4.7±0.3.

The following explanations serve to illustrate the characteristics of the tissue protein.

Determination of the sedimentation coefficients was carried out in an ultra-centrifuge of Messrs. Beckmann (Spinco-apparatus, model E) at 60,000 rev./min. in double sector cells with the aid of UV-scanner technique at 280 nm. As the solvent, a 0.05 M phosphate buffer (pH 6.8), containing 0.2 mole/l NaCl, was used. The protein concentration was adjusted to an optical density (O.D.) of about 3. The sedimentation coefficients were calculated on the basis of water at 20° C.

For determining the molecular weight in the ultracentrifuge, the sedimentation equilibrium method was used. The concentration was adjusted for this purpose to about 1.0 O.D. The determination was effected at 9,000 rev./min. Registration was effected with an ultraviolet optic at 280 nm using a photoelectric scanner.

For determining the molecular weight in SDS-PAA gel, a gel containing 7.5% of polyacrylamide (PAA) and 0.1% of sodium dodecyl sulfate (SDS) was used. As the comparative substance, human placenta-lactogen (HPL) and human albumin as well as their aggregates were used.

For determining the extinction coefficients, the substance was dissolved to a strength of 0.10% (W/v) in distilled water.

The test for the electrophoretic mobility was carried out on cellulose acetate foils of Messrs. Satorius with a sodium diethyl barbiturate buffer of pH 8.6, using the apparatus Microzone R 200 of Messrs. Beckmann Instruments.

Determination of the isoelectric point was made on a column (440 ml) of Messrs. LKB Stockholm. For the glycoprotein test the so-called ampholine mixture had a pH-range of from 4.0 to 6.0.

Determination of the carbohydrates was carried out according to the method described by H. E. Schultze, R. Schmidtberger, H. Haupt, Biochem. Z. 329, page 490 (1958).

The analysis for amido-acids was carried out according to the method described by S. Moore, D. H. Spackmann, W. H. Stein, Anal. Chem. 30, page 1185 (1958), using the liquid chromatograph Multichrom B of Messrs. Beckmann. The amount of ½-cystine present was determined, after oxidation of the protein, with per-formic acid (S. Moore et al., Anal. Chem. 30, page 1185 (1958) and subsequent chromatography (S. Moore, J. Biol. Chem., 238, page 235 (1963)) as cysteinic acid. The content of tryptophan was determined by the direct photometric test method according to H. Edelhoch, Biochemistry 6, page 1948 (1967).

The results of the analysis for amino-acids of PP$_8$ obtained according to the Example are compiled in Table I.

TABLE I

Amino-acid composition of PP$_8$

| | (Mole %) | Variation coefficient (VC) (%) |
|---|---|---|
| Lysine | 7.08 | 3.21 |
| Histidine | 1.49 | 22.07 |
| Arginine | 3.56 | 3.86 |
| Aspartic acid | 10.32 | 6.79 |
| Threonine | 6.08 | 0.96 |
| Serine | 7.88 | 3.99 |
| Glutamic acid | 12.97 | 3.48 |
| Proline | 2.87 | 4.84 |
| Glycine | 6.64 | 2.19 |
| Alanine | 6.41 | 0.65 |
| Cystine/2 | 2.00 | 17.75 |
| Valine | 5.91 | 3.81 |
| Methoionine | 4.67 | 14.45 |
| Isoleucine | 3.10 | 2.01 |
| Leucine | 9.29 | 3.58 |
| Tyrosine | 1.65 | 14.40 |
| Phenylalanine | 6.67 | 7.43 |
| Tryptophan | 1.41 | 2.13 |

The following properties of PP$_8$ were found which may be useful for isolating this tissue protein:

(1) with ammonium sulfate, PP$_8$ is precipitated at pH 7.0, in a saturation of between 40% and 70%, from aqueous solutions;

(2) PP$_8$ is precipitated with water-soluble acridine bases, for example 2-ethoxy-6,9-diaminoacridine lactate (Rivanol ®) at pH-values between 7 and 9 and a concentration of 0.4 to 0.8% w/v.

(3) In preparative electrophoresis, PP$_8$ migrates in the range of the $\alpha_1$-globulins.

(4) In gel-filtration using Sephadex ®, PP$_8$ appears in the range of proteins having molecular weights of between 30 000 to 70 000.

(5) PP$_8$ is adsorbed on weakly basic ion exchangers, for example DEAE-cellulose or DEAE-Sephadex, with use of buffers of low conductivity (about 0–2 mS) and neutral or weakly alkaline pH-values (about pH 7 to 9).

(6) Upon heating (4 hours, 67° C., at pH 5.0) in the presence of salts of aliphatic fatty acids such as caprylate, PP$_8$ remains in solution, as is known from albumin, whereas most of the other proteins are denatured and precipitate.

(7) $PP_8$ can be enriched and isolated from its aqueous solution by immuno-adsorption.

The invention furthermore relates to a process for isolating $PP_8$, which comprises fractionating either an aqueous organ extract, preferably an extract of a placenta, or other aqueous solution which contains this protein, on the basis of the above-described properties. In addition to ammonium sulfate, other neutral salts commonly used in preparative biochemistry can be used for precipitating $PP_8$. Besides acridine bases, water-soluble derivatives of a quinoline base, used in protein fractionation, may be used in the process of the present invention. In view of its electrophoretic behaviour and the molecular weight determined according to the invention, other measures which are suitable for separating an $\alpha_1$-globulin from other plasma or tissue proteins are also suitable for isolating the protein. As regards the molecular weight, various methods of gel-filtration, gel-chromatography by ultra-filtration may be used. This is evident in view of the tendency of $PP_8$ to attach itself to weakly basic ion exchangers and be eluted therefrom again.

$PP_8$ can be isolated by using a selected combination of the above-described measures, which, on the one hand, enrich $PP_8$ and, on the other hand, permit separation of this protein from the other tissue or plasma proteins.

Accordingly, additional objects of the invention are provision of individual steps for enriching $PP_8$ and methods for purifying $PP_8$ which are a combination of the above-mentioned enrichment steps.

The process for the enrichment is characterized in that at least one of the measures 1 to 7 or their chemical or biochemical preparative equivalents are used.

$PP_8$ has antigenic properties; if animals are immunized with this protein, specific antibodies are formed. The proof and the determination of $PP_8$ by immunological methods is important in diagnostics. Obviously, $PP_8$ is a tissue protein which is present in almost all human organs. In the case of diseases which involve tissue disintegration, this protein is present in the blood in a higher concentration. Therefore, the determination of its presence it can be used for the detection of diseases and the control of the course of the disease as well as for the control of the therapy.

The invention is illustrated by the following Example:

EXAMPLE (A) Extraction of placentas and fractionation of the extract 150 kg of deep-frozen human placentas are comminuted in a cutter-mixer and extracted with 150 l of a 0.4% w/v strength NaCl-solution. After separation of the tissue residue by centrifugation, the extract is adjusted to pH 6.0 by means of 20% acetic acid and combined, while stirring, with 33 l of a 3% strength solution of 2-ethoxy-6,9-diaminoacridine-lactate (Rivanol ®, Hoechst AG). The precipitate formed is centrifuged off and discarded. The pH of the supernatant is adjusted to 8.5 with 2 N sodium hydroxide solution and 50 l of a 3% solution of 2-ethoxy-6,9-diaminoacridine-lactate are slowly added, while stirring. During this time, the main quantity of $PP_8$ precipitates; the supernatant is decanted and discarded. The precipitate is stirred with 120 l of water and dissolved by adding 20% strength acetic acid until a pH-value of 5.0 is attained. After having stirred for 2 hours, 5% w/v of NaCl are added in order to displace the acridine base (Rivanol ®) and the pH-value is adjusted to 7.0. The Rivanol-hydrochloride that has separated is filtered off. The protein-containing filtrate is combined with 0.20 kg of sodium caprylate (dissolved in 15 l of water) and the pH value of the solution is adjusted to 5.0 by adding 20% strength acetic acid. The solution is then heated to 67° C., while stirring continuously, and kept at this temperature for 4 hours. Subsequently, it is cooled to 10°–15° C. Most of the proteins are denatured by this heat treatment and precipitate; albumin and the protein $PP_8$ remain in solution. The precipitate is filtered off and, after neutralization, the solution is concentrated on an ultrafilter to a concentration of about 20% of protein. Yield: 3.5 l, containing 5 to 10 mg of $PP_8$ per 100 ml. From this solution, $PP_8$ was further enriched by immuno-adsorption and then isolated.

(B) Enrichment of $PP_8$ by immuno-adsorption

1. Preparation of the immuno-adsorbent 300 ml of anti-$PP_8$ serum from a rabbit are dialyzed against a 0.02 M phosphate buffer (pH 7.0) and chromatographed on DEAE-cellulose to separate the immuno-globulins. The immunoglobulin fraction (3.75 g of protein) is then reacted with 375 g of especially purified agarose in spherical form (Sepharose ® 4 B of Pharmacia, Uppsala, Sweden) which had been activated with 46.9 g of cyanogen bromide and is thus bound covalently onto a carrier.

This process is described by Axen, R., Porath, J., Ernbach, S., Nature, 214, 1302 (1967).

The placenta protein $PP_8$ can be isolated from its solutions, especially from its $PP_8$-enriched placenta extract fractions, by means of the immuno-adsorbent prepared in this manner.

2. Carrying out the immuno-adsorption

The immuno-adsorbent is suspended in a 0.1 M Tris-HCl buffer (pH 8.0), containing 1.0 mole/l of NaCl and 0.1% of $NaN_3$ (hereinafter referred to as buffer solution I), then filled into a column for chromatography (5.5×20 cm) and rinsed with the buffer I. Then, 450 ml of the $PP_8$-containing solution are slowly passed through the column, whereby $PP_8$ is bound immuno-adsorptively. The column is thoroughly washed with buffer I and the adsorbed protein is eluted with a 3 M potassium thiocyanate solution. The $PP_8$-containing eluates are dialyzed against the buffer solution I and concentrated to about 10 ml in an ultrafilter. Yield per adsorption: 10 mg of $PP_8$.

Directly after the elution of $PP_8$, the adsorbent in the column is neutralized with the buffer solution I and washed thoroughly; it can then be used again for the immuno-adsorptive fixation of $PP_8$.

(C) High Purification of $PP_8$

The protein obtained by immuno-adsorption is often contaminated by unspecifically bound serum proteins (mainly albumin). Separation of the main quantity of these accompanying proteins is made, for example, by gel-filtration on Sephadex G-150. $PP_8$ passes and leaves the column directly after the albumin. The remaining serum proteins can be removed by inverse or negative immuno-adsorption, i.e. with the aid of carrier-bound antibodies of the serum proteins present as contamination.

What is claimed is:

1. An isolated, enriched tissue protein obtainable by fractionating an aqueous organ extract, the amino-acid composition of said tissue protein being:

| Amino acid | Mole % | Variation coefficient (%) |
|---|---|---|
| Lysine | 7.08 | 3.21 |
| Histidine | 1.49 | 22.07 |
| Arginine | 3.56 | 3.86 |
| Aspartic acid | 10.32 | 6.79 |
| Threonine | 6.08 | 0.96 |
| Serine | 7.88 | 3.99 |
| Glutamic acid | 12.97 | 3.48 |
| Proline | 2.87 | 4.84 |
| Glycine | 6.64 | 2.19 |
| Alanine | 6.41 | 0.65 |
| Cystine/2 | 2.00 | 17.75 |
| Valine | 5.91 | 3.81 |
| Methoionine | 4.67 | 14.45 |
| Isoleucine | 3.10 | 2.01 |
| Leucine | 9.29 | 3.58 |
| Tryosine | 1.65 | 14.40 |
| Phenylalanine | 6.67 | 7.43 |

-continued

| Amino acid | Mole % | Variation coefficient (%) |
|---|---|---|
| Tryptophan | 1.41 | 2.13 | and said tissue protein having
 (a) a protein proportion of 96±3%,
 (b) a carbohydrate content of 4.1±0.95%, of which 3.15±0.5% are hexoses, 0.61±0.2% is hexoseamine, 0.11±0.05% is fucose and 0.23±0.20 is neuraminic acid;
 (c) a sedimentation coefficient $S_{20\ w}$ of 3.7±0.3 S;
 (d) a molecular weight of 45 000±5 000, determined in the ultracentrifuge;
 (e) a molecular weight of 55 000±5 000 determined in sodium dodecylsulfate (SDS)-containing polyacrylamide gel;
 (f) an extinction coefficient $E_{1\ cm}1\%$ (280 mm) of 8.1±1.0;
 (g) an electrophoretic mobility in the range of the alpha$_1$-globulins; and
 (h) an isoelectric point of 4.7±0.3.

2. A tissue protein as defined in claim 1, wherein said aqueous organ extract is an extract of human placenta.

* * * * *